(12) United States Patent
Franks et al.

(10) Patent No.: US 7,442,383 B2
(45) Date of Patent: Oct. 28, 2008

(54) USE OF XENON FOR THE CONTROL OF NEUROLOGICAL DEFICITS ASSOCIATED WITH CARDIOPULMONARY BYPASS

(75) Inventors: Nicholas Peter Franks, London (GB); Mervyn Maze, London (GB)

(73) Assignee: Protexeon Limited, Aldwych, London (GB)

( * ) Notice: Subject to any disclaimer, the term of this patent is extended or adjusted under 35 U.S.C. 154(b) by 0 days.

(21) Appl. No.: 10/512,758

(22) PCT Filed: May 1, 2003

(86) PCT No.: PCT/GB03/01867

§ 371 (c)(1),
(2), (4) Date: Oct. 26, 2004

(87) PCT Pub. No.: WO03/092707

PCT Pub. Date: Nov. 13, 2003

(65) Prior Publication Data

US 2005/0238726 A1    Oct. 27, 2005

(30) Foreign Application Priority Data

May 1, 2002    (GB) .................................. 0209998.4

(51) Int. Cl.
*A61F 2/00*    (2006.01)
(52) U.S. Cl. ................... 424/423; 514/816; 514/958
(58) Field of Classification Search ................. 424/423; 514/816, 958
See application file for complete search history.

(56) References Cited

U.S. PATENT DOCUMENTS 6,197,323 B1 *    3/2001    Georgieff ................... 424/423

FOREIGN PATENT DOCUMENTS

| WO | WO 00/53192 | | 9/2000 |
| WO | WO-00/53192 | * | 9/2000 |
| WO | WO 00/76545 | | 12/2000 |
| WO | WO 01/08692 | | 2/2001 |

OTHER PUBLICATIONS

Johnsson et al. Ann Thorac Surg 1991, 51, 579-84.*
Gardner et al., Stroke Following Coronary Artery Bypass Grafting: A Ten-Year Study, The Annals of Thoracic Surgery, vol. 40, No. 6, Dec. 1985, XP009015316.
Grocott et al., Neurological Injury During Cardiopulmonary Bypass in the Rat, Perfusion 2001; 16: 75-91, XP009015397.
Ma, et al., Xenon Attenuates Cardiopulmonary Bypass-Induced Neurologic and Neurocognitive Dysfunction in the Rat, 2002 ASA Meeting Abstracts, Oct. 2002, XP-001154264.

* cited by examiner

*Primary Examiner*—Johann Richter
*Assistant Examiner*—Ernst V Arnold
(74) *Attorney, Agent, or Firm*—Kenyon & Kenyon LLP (57) ABSTRACT

The present invention relates to methods of controlling neurological deficits in patients who have undergone cardiopulmonary bypass (CPB) by administering xenon to said patients.

14 Claims, 6 Drawing Sheets

USE OF XENON FOR THE CONTROL OF NEUROLOGICAL DEFICITS ASSOCIATED WITH CARDIOPULMONARY BYPASS

This application is a 371 of PCT/GB03/01867 filed on May 1, 2003.

The present invention relates to methods of controlling neurological deficits in patients who have undergone cardiopulmonary bypass (CPB).

CPB refers to the placement of a patient onto extracorporeal membrane oxygenation to bypass the heart and lungs as, for example, in open heart surgery. The device takes blood from the body, diverts it through a heart-lung machine (a pump oxygenator) which oxygenates the blood prior to returning it to the systemic circulation under pressure. The machine does the work both of the heart (pump blood) and the lungs (supply red blood cells with oxygen, remove carbon dioxide), thereby allowing the surgeon to perform primary heart surgery on a temporarily non-functioning heart.

However, since the advent of CPB, cerebral injury after cardiac surgery has been widely documented in humans (Gardner T et al, Ann Thorac Surg 1985, 40:574-81; Tuman K J et al, J Thorac Cardiovasc Surg 1992, 104:1510-7; Newman M et al, Multicenter Study of Perioperative Ischaemia Research Group, Circulation 1996, 94II74-80). Clinical manifestations of this injury vary from frank stroke to subtle neurocognitive dysfunction (Roach G et al, N Engl J Med 1996, 335:1857-63; Newman M et al, N Engl J Med 2001, 344:395-402). As used herein the terms "neurobehavioural" and "neurological" are used interchangeably.

More specifically, drawbacks associated with CPB may include neurological deficits such as neuromotor, neurocognitive, or spatial memory deficits. Typically, these deficits are apparent during the first few days after the patient has undergone CPB.

The present invention thus seeks to provide a neuroprotectant that is capable of controlling and/or alleviating one or more of the drawbacks associated with CPB.

STATEMENT OF INVENTION

A first aspect of the invention relates to the use of xenon in the preparation of a medicament for controlling one or more neurological deficits associated with CPB.

A second aspect of the invention provides a method of providing neuroprotection in a mammal, the method comprising administering to the mammal a therapeutically effective amount of xenon during CPB.

A third aspect of the invention provides a method of controlling one or more neurological deficits associated with CPB in a mammal, said method comprising the steps of:
  (i) administering xenon to said mammal prior to the commencement of CPB;
  (ii) administering xenon to said mammal during CPB; and
  (iii) administering xenon to said mammal after CPB has been concluded.

DETAILED DESCRIPTION

Xenon is a chemically inert gas whose anaesthetic properties have been known for over 50 years (Lawrence J H et al, J. Physiol. 1946; 105:197-204). Since its first use in surgery (Cullen S C et al, Science 1951; 113:580-582), a number of research groups have shown it has an excellent pharmacological profile, including the absence of metabolic by-products, profound analgesia, rapid onset and recovery, and minimal effects on the cardiovascular system (Lachmann B et al, Lancet 1990; 335:1413-1415; Kennedy R R et al, Anaesth. Intens. Care 1992; 20:66-70; Luttropp H H et al, Acta Anaesthesiol. Scand. 1994; 38:121-125; Goto T et al, Anesthesiology 1997; 86:1273-1278; Marx T et al, Br. J. Anaesth. 1997; 78:326-327). However, until recently, the molecular mechanisms underlying the clinical activity of xenon have remained elusive.

Previous studies by the applicant have revealed that xenon has neuroprotective properties. In particular, WO 01/08692, the contents of which are incorporated herein by reference, relates to the use of xenon as a neuroprotectant and/or as an inhibitor of synaptic plasticity. However, there is no teaching or suggestion in the prior art that xenon would be effective as a neuroprotectant in the context of the presently claimed invention.

As used herein, the term "neuroprotectant" means an agent that is capable of providing neuroprotection, i.e., protecting a neural entity, such as a neuron, at a site of injury, for example, an ischaemic injury or traumatic injury.

In a preferred embodiment, the xenon is an NMDA antagonist.

The term "antagonist" is used in its normal sense in the art, i.e., a chemical compound which prevents functional activation of a receptor by its natural agonist (glutamate, in this case).

The NMDA (N-methyl-D-aspartate) receptor is a major subclass of glutamate receptor and glutamate is believed to be the most important excitatory neurotransmitter in the mammalian central nervous system. Importantly, activation of the NMDA receptor has been shown to be the central event which leads to excitotoxicity and neuronal death in many disease states, as well as a result of hypoxia and ischaemia following head trauma, stroke and following cardiac arrest.

It is known in the art that the NMDA receptor plays a major role in the synaptic plasticity which underlies many higher cognitive functions, such as memory and learning, as well as in certain nociceptive pathways and in the perception of pain (Collingridge et al, The NMDA Receptor, Oxford University Press, 1994). In addition, certain properties of NMDA receptors suggest that they may be involved in the information-processing in the brain which underlies consciousness itself.

NMDA receptor antagonists are therapeutically valuable for a number of reasons. Firstly, NMDA receptor antagonists confer profound analgesia, a highly desirable component of general anaesthesia and sedation. Secondly, NMDA receptor antagonists are neuroprotective under many clinically relevant circumstances (including ischemia, brain trauma, neuropathic pain states, and certain types of convulsions). Thirdly, NMDA receptor antagonists confer a valuable degree of amnesia.

However, there are a number of drawbacks associated with many conventional NMDA receptor antagonists. These include the production of involuntary movements, stimulation of the sympathetic nervous system, induction of neurotoxicity at high doses (which is pertinent since NMDA receptor antagonists have low potencies as general anaesthetics), depression of the myocardium, and proconvulsions in some epileptogenic paradigms e.g., "kindling" (Wlaz P et al, Eur. J. Neurosci. 1994; 6:1710-1719). In particular, there have been considerable difficulties in developing new NMDA receptor antagonists that are able to cross the blood-brain barrier. This factor has also limited the therapeutic applications of many known NMDA antagonists.

Unlike many other NMDA antagonists, xenon is able to rapidly equilibrate with the brain by diffusing across the blood brain barrier. A further advantage of using xenon as an NMDA antagonist is that the molecule is an inert, volatile gas that can be rapidly eliminated via respiration.

In a particularly preferred embodiment, the xenon controls one or more neurological deficits associated with CPB.

As used herein, the term "controlling/control of neurological deficits" refers to reducing the severity of one or more neurological deficits as compared to a subject having undergone CPB in the absence of xenon.

In an even more preferred embodiment, the neurological deficit may be a neuromotor or neurocognitive, deficit. As used herein the term "neuromotor deficit" is to given its meaning as understood by the skilled artisan so as to include deficits in strength, balance and mobility. Similarly, the term "neurocognitive deficit" is given its meaning as understood by the skilled artisan so as to include deficits in learning and memory. Such neurocognitive deficits may typically be assessed by well-established criteria such as the short-story module of the Randt Memory Test [Randt C, Brown E. Administration manual: Randt Memory Test. New York: Life Sciences, 1983], the Digit Span subtest and Digit Symbol subtest of the Wechsler Adult Intelligence Scale-Revised [Wechsler D. The Wechsler Adult Intelligence Scale-Revised (WAIS-R). San Antonio, Tex.: Psychological Corporation, 1981.], the Benton Revised Visual Retention Test [Benton A L, Hansher K. Multilingual aphasia examination. Iowa City: University of Iowa Press, 1978] and the Trail Making Test (Part B) [Reitan R M. Validity of the Trail Making Test as an indicator of organic brain damage. Percept Mot Skills 1958; 8:271-6]. Other suitable neuromotor and neurocognitive tests are described in Combs D, D'Alecy L: Motor performance in rats exposed to severe forebrain ischemia: Effect of fasting and 1,3-butanediol. Stroke 1987; 18: 503-511 and Gionet T, Thomas J, Warner D, Goodlett C, Wasserman E, West J: Forebrain ischemia induces selective behavioral impairments associated with hippocampal injury in rats. Stroke 1991; 22: 1040-1047).

Preferably, the xenon is administered in combination with a pharmaceutically acceptable carrier, diluent or excipient.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers and dyes may be provided in the pharmaceutical composition. Examples of preservatives include sodium benzoate, sorbic acid and esters of p-hydroxybenzoic acid. Antioxidants and suspending agents may be also used.

The xenon may also be administered in combination with another pharmaceutically active agent. The agent may be any suitable pharmaceutically active agent including anaesthetic or sedative agents which promote GABAergic activity. Examples of such GABAergic agents include isoflurane, propofol and benzodiazapines.

The xenon may also be administered in combination with other active ingredients such as L-type calcium channel blockers, N-type calcium channel blockers, substance P antagonists, sodium channel blockers, purinergic receptor blockers, or combinations thereof.

The xenon may be administered by any suitable delivery mechanism, or two or more suitable delivery mechanisms.

In one particularly preferred embodiment, the xenon is administered by perfusion. In the context of the present invention, the term "perfusion" refers to the introduction of an oxygen/xenon mixture into, and the removal of carbon dioxide from, a patient using a specialised heart-lung machine. In general terms, the heart-lung machine replaces the function of the heart and lungs and provides a bloodless, motionless surgical field for the surgeon. The perfusionist ventilates the patient's blood to control the level of oxygen and carbon dioxide. In the context of the present invention, the perfusionist also introduces xenon into the patient's blood. The perfusionist then propels the blood back into the arterial system to provide nutrient blood flow to all the patient's vital organs and tissues during heart surgery.

In another highly preferred embodiment, the xenon is administered by inhalation. More preferably, the xenon is administered by inhalation of a 70-30% v/v xenon/oxygen mixture.

Xenon is administered to a patient in a manner familiar to those skilled in the art. Patients undergoing CPB are suitably ventilated and xenon may be administered in the same or a parallel line to the oxygen/$CO_2$.

In one particularly preferred embodiment, the xenon or xenon/oxygen mixture is administered using a combination inhalation/heart-lung machine as described in co-pending PCT applications of Air Products and Chemicals, Inc. [Agent's Attorney Reference Numbers P8942WO, P8943WO and P8944WO all filed on 1 May 2003, claiming priority from UK Patent Applications Nos. 0210021.2, 0210022.0 and 0210023.8 respectively, all filed on 1 May 2002), the contents of which are herein incorporated by reference.

In yet another preferred embodiment, the xenon is administered in liquid form. Preferably, the liquid is administered in the form of a solution or an emulsion prepared from sterile or sterilisable solutions, which may be injected intravenously, intraarterially, intrathecally, subcutaneously, intradermally, intraperitoneally or intramuscularly.

In one particularly preferred embodiment, the xenon is administered in the form of a lipid emulsion. The intravenous formulation typically contains a lipid emulsion (such as the commercially available Intralipid®10, Intralipid®20, Intrafat®, Lipofundin®S or Liposyn® emulsions, or one specially formulated to maximise solubility) which sufficiently increases the solubility of the xenon to achieve the desired clinical effect. Further information on lipid emulsions of this sort may be found in G. Kleinberger and H. Pamperl, Infusionstherapie, 108-117 (1983) 3.

The lipid phase of the present invention which dissolves or disperses the gas is typically formed from saturated and unsaturated long and medium chain fatty acid esters containing 8 to 30 carbon atoms. These lipids form liposomes in aqueous solution. Examples include fish oil, and plant oils such as soya bean oil, thistle oil or cottonseed oil. The lipid emulsions of the invention are typically oil-in-water emulsions wherein the proportion of fat in the emulsion is conventionally 5 to 30% by weight, and preferably 10 to 20% by weight. Oil-in-water emulsions of this sort are often prepared in the presence of an emulsifying agent such as a soya phosphatide.

The lipids which form the liposomes of the present invention may be natural or synthetic and include cholesterol, glycolipids, sphingomyelin, glucolipids, glycosphingolipids, phosphatidylcholine, phosphatidylethanolamine, phosphatidylserine, phosphatidyglycerol, phosphatidylinositol.

The lipid emulsions of the present invention may also comprise additional components. These may include antioxidants, additives which make the osmolarity of the aqueous phase surrounding the lipid phase isotonic with the blood, or polymers which modify the surface of the liposomes.

It has been established that appreciable amounts of xenon maybe added to a lipid emulsion. Even by the simplest means, at 20° C. and normal pressure, xenon can be dissolved or dispersed in concentrations of 0.2 to 10 ml or more per ml of emulsion.

The concentration of dissolved gas is dependent on a number of factors, including temperature, pressure and the concentration of lipid.

The lipid emulsions of the present invention may be loaded with gaseous xenon. In general, a device is filled with the emulsion and anaesthetics as gases or vapours passed through sintered glass bubblers immersed in the emulsion. The emulsion is allowed to equilibrate with the anaesthetic gas or vapour at a chosen partial pressure. When stored in gas tight containers, these lipid emulsions show sufficient stability for the anaesthetic not to be released as a gas over conventional storage periods.

The lipid emulsions of the present invention may be loaded so that the xenon is at the saturation level. Alternatively, the xenon may be present in lower concentrations, provided, for example, that the administration of the emulsion produces the desired pharmaceutical activity.

The concentration of xenon employed in the invention may be the minimum concentration required to achieve the desired clinical effect. It is usual for a physician to determine the actual dosage that will be most suitable for an individual patient, and this dose will vary with the age, weight and response of the particular patient. There can, of course, be individual instances where higher or lower dosage ranges are merited, and such are within the scope of this invention.

A further aspect of the present invention relates to the timing of xenon administration.

In one preferred embodiment, xenon is administered to said mammal during CPB.

In another preferred embodiment, xenon is administered after CPB has been concluded.

In yet another preferred embodiment, xenon is administered prior to the commencement of CPB.

In one embodiment, the xenon is administered at least during the period of CPB, i.e. whilst the patient is attached to the heart lung machine. In a further embodiment, xenon administration is commenced prior to CPB and/or continued for a period after CPB has been concluded. It is preferable that xenon administration occurs both prior to and during CPB. In all embodiments administration may optionally be continued after CPB has been concluded.

In one especially preferred embodiment of the invention, xenon is administered to the mammal
(i) prior to commencement of CPB;
(ii) during CPB; and
(iii) after CPB has been concluded.

In more detail, the steps prior to, during, and after CPB are as follows. After sternotomy, the patient is systemically anticoagulated and the right atrium and aorta are cannulated. Following cannulation, venous blood is diverted from the heart and lungs and returned to the CPB circuit for oxygenation, carbon dioxide extraction and xenon administration. At the conclusion of CPB, the patient is decannulated and the systemic anticoagulation is reversed. Once hemostasis is secured, the sternum is closed.

Preferably, the xenon is administered prior to commencement of CPB during preparatory surgery, for example, during sternotomy and/or whilst the patient is systemically anticoagulated and the right atrium and aorta are cannulated.

Preferably, the xenon is administered in step (iii) after the heart has been restarted and/or during the final stages of surgery. In one preferred embodiment, the xenon is administered at the conclusion of CPB, when the patient is decannulated and the systemic anticoagulation is reversed, and/or once hemostasis is secured and the sternum is closed.

In one particularly preferred embodiment of the invention, the temperature of the mammal to which the xenon is administered is controlled. Preferably, the temperature is decreased to below normal body temperature. Typically, the temperature is lowered from about 1° C. to about 10° C., more preferably from about 1° C. to about 5° C. below normal body temperature.

A third aspect of the invention relates to a method of controlling one or more neurological deficits associated with CPB in a mammal, said method comprising the steps of:
(i) administering xenon to said mammal prior to the commencement of CPB;
(ii) administering xenon to said mammal during CPB; and
(iii) administering xenon to said mammal after CPB has been concluded.

Preferred embodiments for the second and third aspects of the invention are identical to those described above for the first aspect.

Preferably, the xenon is administered in step (i) by inhalation or by intravenous injection, more preferably by inhalation.

Preferably, the xenon is administered in step (iii) by inhalation or by intravenous injection, more preferably by inhalation.

Preferably, step (ii) comprises administering xenon to the mammal by perfusion using a specialised heart lung machine.

The present invention is also applicable to the treatment of animals. In this regard, the invention further relates to the use of xenon in combination with a veterinarily acceptable diluent, excipient or carrier.

For veterinary use, the xenon is typically administered in accordance with normal veterinary practice and the veterinary surgeon will determine the dosing regimen and route of administration which will be most appropriate for a particular animal.

A further aspect of the invention provides a method of controlling one or more neurological deficits associated with CPB in a mammal, the method comprising administering to the mammal a therapeutically effective amount of xenon.

Preferably, the xenon is administered in combination with a pharmaceutically acceptable carrier, diluent or excipient.

Even more preferably, the xenon reduces the level of activation of the NMDA receptor.

A BRIEF DESCRIPTION OF THE DRAWINGS

The present invention is further described by way of example, and with reference to the following figures wherein:

FIG. 1 shows a schematic diagram of the experimental protocol. Neurologic outcome was assessed after CPB using standardised functional testing. Neurocognitive outcome, defined as the time (or latency) to find a submerged platform in a Morris water maze (an indicator of visual-spatial learning and memory), was evaluated daily from post CPB days 3-12.

FIG. 4 shows neurocognitive outcome as evaluated daily (3-12) after cardiopulmonary bypass (CPB) by visual-spatial learning and memory with the Morris water maze. The results are the sum of four latencies for each rat on each day (latency is defined as the time for animals to find the submerged platform starting at a different quadrant on each trial). Data are Mean±SEM, with n=10). ANOVA shows that Sham, CPB+MK801 or CPB+Xe group have a significant statistically difference when compared with CPB group respectively (CPB vs Sham: F=18.2, p<<0.0001; CPB vs CPB+MK801: F=20.7, p<0.0001; CPB vs CPB+Xe: F=21.6, p <0.0001). Repeated measures with Student-Newman-Keuls, followed by analysis of variance, shows a significant difference when compared with CPB group at days 3 and 4 post-CPB.

FIG. 6 shows LDH release (normalised) against xenon concentration (% atm) at each temperature.

EXAMPLES

Surgical Preparation and Cardiopulmonary Bypass (CPB)

The methodology of the CPB model used in the current study has been previously reported (Anesthesiology 2001, 95:1485-91). Briefly, anesthesia was induced in male Sprague-Dawley rats (12-14 weeks, 350-380 gm; Harlan, Indianapolis, Ind.) with 5% isoflurane in oxygen-enriched air in a plastic box. Following orotracheal intubation with a 14-gauge cannula, the lungs were mechanically ventilated (40% $O_2$/balance $N_2$) to maintain a $PaCO_2$ of 36-42 mmHg. During surgical preparation, anesthesia was maintained with 2.0-2.5% isoflurane and the rectal and pericranial temperatures were monitored and servo-controlled at 37.5±0.1° C. (YSI 400 series thermistor and 73ATA Indicating controller; YSI, Yellow Springs, Ohio) with a heating blanket and convective forced-air heating system. The superficial caudal epigastric artery, a branch of a femoral artery, was cannulated with PE-10 tubing for monitoring mean arterial pressure (MAP). During cardiopulmonary bypass (CPB) rats were anesthetized with fentanyl (30 μg/kg, i.v.), midazolam (0.4 mg/kg, i.v.) and atracurium (0.5 mg/kg, i.v.) as a bolus of injection and followed by a continuous infusion of the mixture of three with a syringe pump (2.5 μg/kg/min for fentanyl, 0.03 mg/kg/min for midazolam and 0.08 mg/kg/min for atracurium). Pilot studies had been confirmed that with this anesthetic regimen, the animals had enough depth of anesthesia during CPB. Blood was drained via a 4.5 Fr multi-orifice cannula inserted into the internal jugular vein via a neck incision and advanced until the tip of the cannula was placed near the junction of the inferior vena cava and right atrium; Blood was returned from the CPB circuit via a 20-gauge 1.1-inch catheter sited in a ventral tail artery (ventral side).

Figure 1:
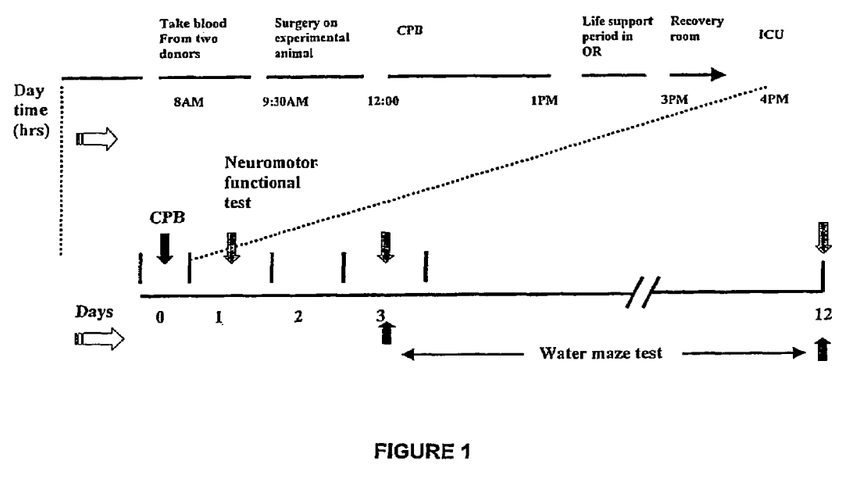
Figure 2:
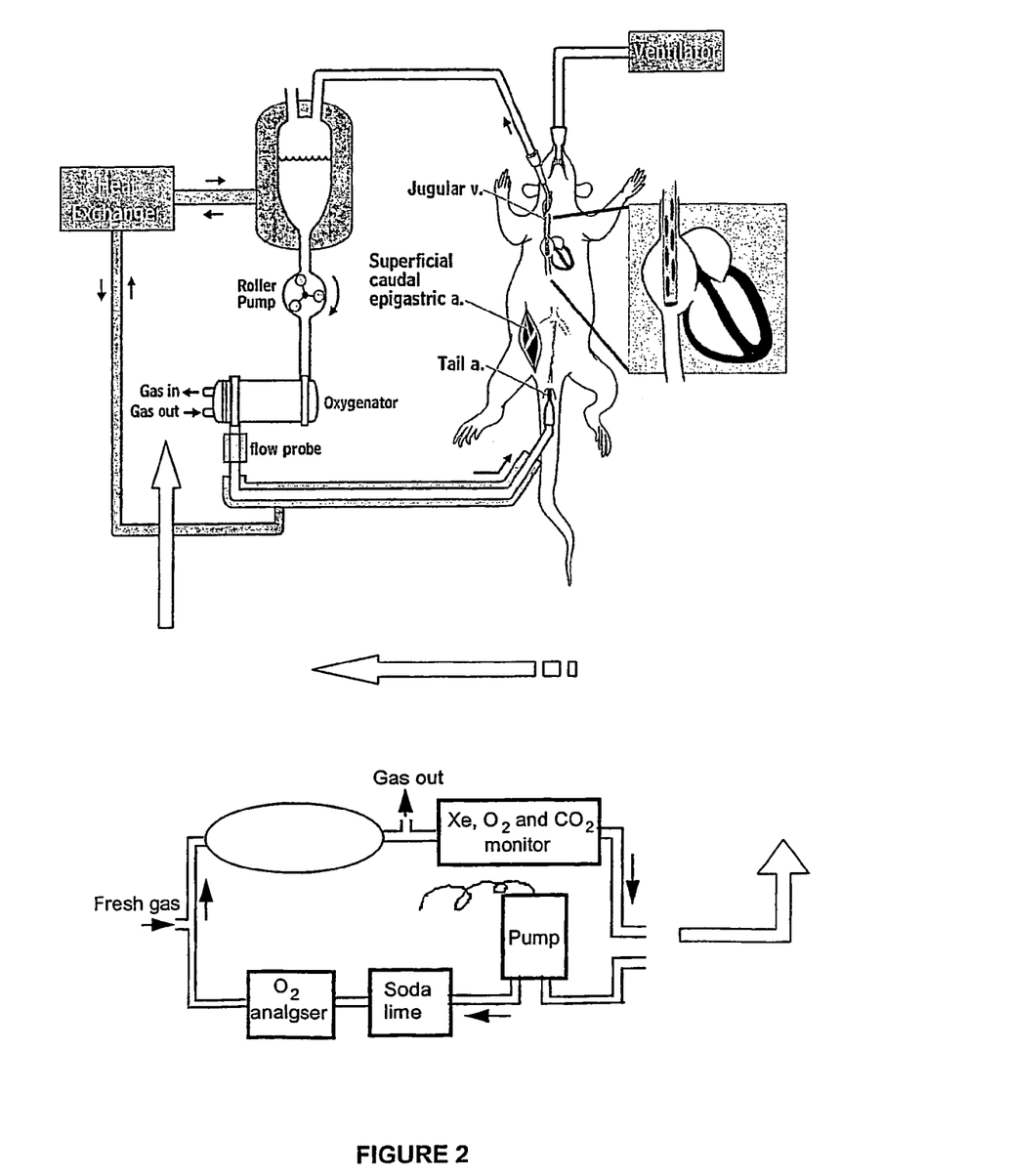
FIG. 2 shows a schematic diagram of rat CPB model and xenon gas delivery system.

The CPB circuit (FIG. 2) consisted of a venous reservoir, a peristaltic pump and a membrane oxygenator, all of which were connected via 1.6 mm internal diameter silicone tubing (Tygon®; Cole-Parmer Instrument Co., Vernon Hills, Ill.). The CPB circuit was primed with approximately 40 ml of whole blood obtained prior to the start of the experiment from two heparinized (100IU/rat, i.v.) donor rats (275-320 gm) which were exsanguinated under isoflurane anesthesia. The drained blood traversed a warmed venous reservoir (jacketed with circulating water from a heat pump) to a peristaltic pump (Masterflex®; Cole-Parmer Instrument Co., Vernon Hills, Ill.) to a membrane oxygenator (a modified Cobe Micro® neonatal oxygenator with a surface area of 0.33 $m^2$; Cobe Cardiovascular, Inc., Arvada, Colo.). A closed-circuit gas delivery system fed the appropriate gas into the oxygenator after which blood was inflsed back into the rat. An in-line flow probe (2N806 flow probe and T208 volume flowmeter; Transonics Systems, Inc., Ithaca, N.Y.) was used to continuously measure CPB flow. Arterial line inflow temperature was maintained at 37.5° C. using a circulating water bath system. The venous oxygen saturation from the venous return line was measured continuously using an Oximetrix® Monitor and Opticath® Catheter (Abbot Laboratories, North Chicago, Ill.). Arterial blood gases were performed using a IL 1306 blood gas analyzer (Instrument Laboratories, Inc., Lexington, Mass.) with hemoglobin determined using an OSM3 Hemoximeter® (Radiometer Inc., Copenhagen, Denmark).

Experimental Protocol

After complete of all surgical procedures as described as above, rats were randomly divided into one of four groups. Sham group: rats (n=10) were cannulated but did not undergo CPB. CPB group: rats (n=10) were subjected to 60 min of non-pulsatile CPB with a membrane oxygenator receiving a mixture of 30% $O_2$ and 65% $N_2$. CPB+MK801 group: rats (n=10) received MK801 (0.15 mg/kg, i.v.) 15 min prior to 60 min of CPB with similar concentrations of gases as in group 2. The dose of MK801 was chosen from pilot studies, in which its side effect can be kept at minmal level. CPB+Xenon group: rats (n=10) underwent 60 min of CPB with a membrane oxygenator receiving a mixture of 30% $O_2$ and 60% xenon.

Physiological Parameters

There were no significant differences in mean arterial pressure and flow rates in the three CPB groups. The pH and blood gas measurements were maintained within normal limits throughout. During CPB, the mixed venous oxygen saturation sampled at the venous reservoir is lower than normal, with no significant differences among the three CPB groups. Hemoglobin gradually decreased in the sham group (possibly due to blood sampling), while in each of the three CPB groups it gradually increased to near baseline level 120 min after CPB with no significant differences among the three groups with CPB. No statistical significant difference was found for blood glucose among the four groups. The rectal and pericranial temperatures were well maintained near 37.5° C. except for a brief period between 10-20 min into CPB (probably due to the inflsion of relatively cold blood form the circuit); no significant differences were noted among the three CPB groups. The animals' body weight decreased to a nadir on the $3^{rd}$ postoperative day; thereafter it increased to above baseline by the end of the experiment on the $12^{th}$ postoperative day. No differences were found among the four groups for weight.

Neurologic and Neurocognitive Test

At $1^{st}$, $3^{rd}$ and $12^{th}$ postoperative day, all animals underwent standardized functional neurologic testing using an established protocol that included assays of prehensile traction, strength, and balance beam performance which was graded on a zero to nine scale (best score=9) (Combs D, D'Alecy L: Motor performance in rats exposed to severe forebrain ischemia: Effect of fasting and 1,3-butanediol. Stroke 1987; 18: 503-511 Gionet T, Thomas J, Warner D, Goodlett C, Wasserman E, West J: Forebrain ischemia induces selective behavioral impairments associated with hippocampal injury in rats. Stroke 1991; 22: 1040-1047).

In addition to the neurologic evaluation, behavioral test using the Morris water maze by a computerized video tracking system (EthoVision®; Noldus, Wageningen, The Netherlands) to evaluate neurocognitive outcome was instituted on the third post-operative day by an investigator blinded to group assignment (Morris R: Developments of a water-maze procedure for studying spatial learning in the rat. J Neurosci Methods 1984; 11: 47-60). Briefly, the Morris water maze consisted of a 1.5 m. diameter, 30 cm. deep pool of water (26.5±0.2° C.) with a submerged (one cm. below surface) hidden platform in one quadrant. Rats were placed in the water in a dimly lit room with multiple extra maze visual clues. The time to locate the submerged platform (defined as the latency) was measured to test for of impairment in visual-spatial learning and memory. Rats underwent daily testing in the water maze with four trials per testing period, each limited to a 90-second water exposure. Each of the trials was begun from a separate quadrant. The testing was consecutively repeated for 10 days.

General Behavioural Changes

All animals which had received MK801 exhibited hyperactivity, head weaving and related disturbances of motor coordination which lasted for 1-2 hrs after they emerged from anesthesia. All animals were able to drink and to eat after emergence.

Neuromotor Functional Testing

Figure 3:
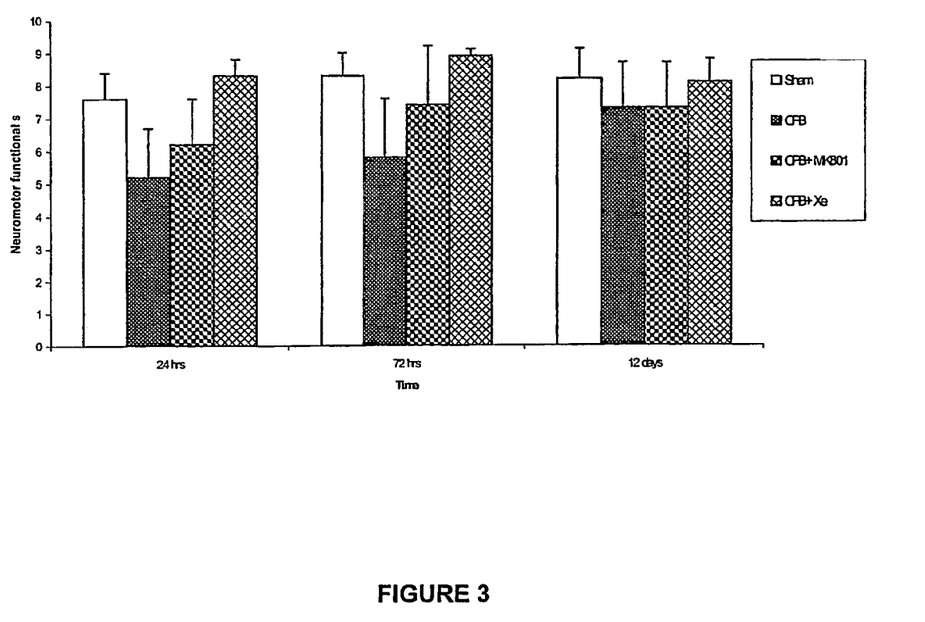
FIG. 3 shows neuromotor functional scoring after 24 hours, 72 hours and 12 days for sham, CPB, CPB+MK801 and CPB+Xe groups.

The CPB group had worse neurologic outcome compared with either the sham group or CPB+Xenon group on the $1^{st}$ and $3^{rd}$ postoperative days [on the $1^{st}$ day: 5.2±1.5 vs 7.6±0.8 (p<0.01) or 8.3±0.5 (p<0.001); on the $3^{rd}$ day: 5.8±1.8 vs 8.3±0.7 (p<0.05) or 8.9±0.2 (p<0.001)], but no difference was found between CPB group and CPB+MK801 group (on the $1^{st}$ day: 5.2±1.5 vs 6.2±1.4, p>0.05; on the $3^{rd}$ day: 5.8±1.8 vs 7.4±1.8, p>0.05). On the $12^{th}$ postoperative day, no difference was found among the four groups (FIG. 3). Qualitative analysis of the individual components within the functional neurological testing suggested that this difference was predominantly attributable to worse performance on the balance beam and prehensile traction ability (data not shown).

Morris Water Maze Testing

The latencies, denoting the time taken by animals to find platform based on four trials of each day, were longer in the CPB group compared to the Sham, CPB+MK801 and CPB+Xe groups.

Figure 4:
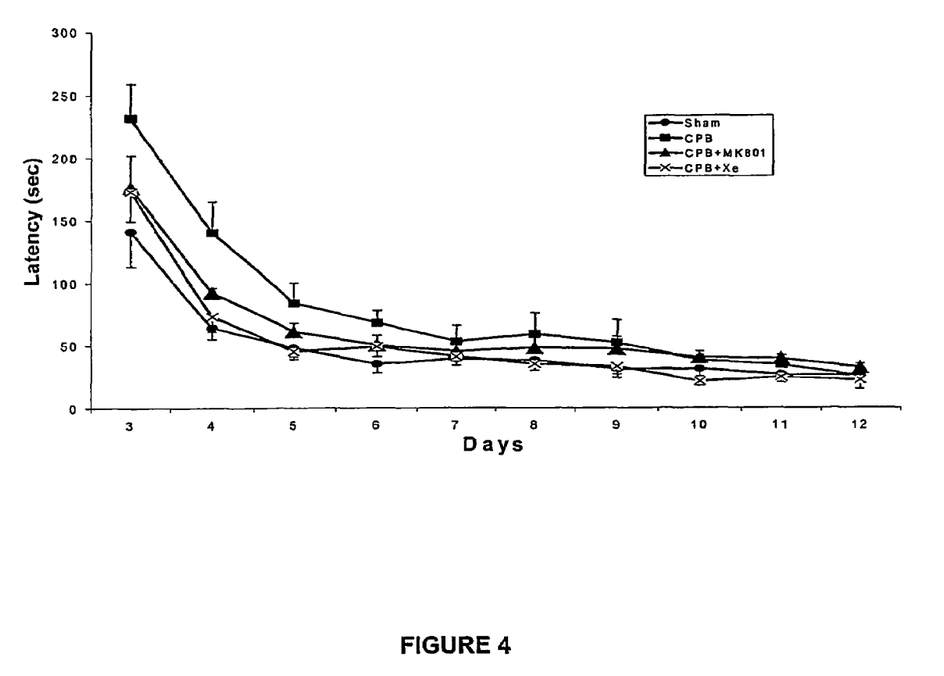
Figure 5:
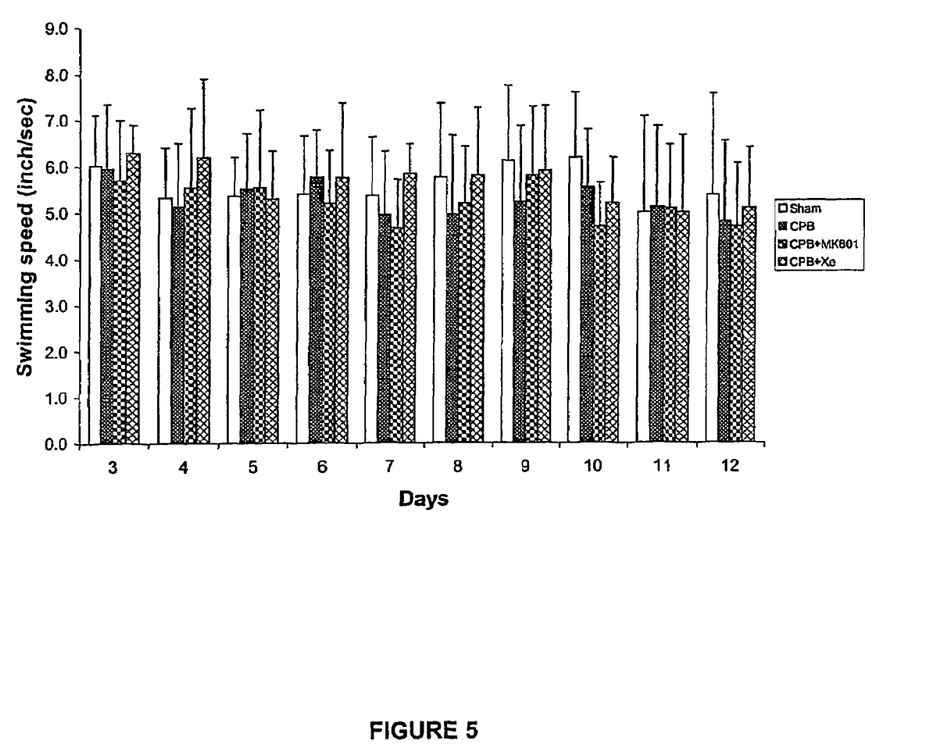
FIG. 5 shows swimming speed during the Morris water maze test for sham, CPB, CPB+MK801 and CPB+Xe groups. Swimming speeds as recorded by a computerised video tracking system measured daily (3-12 d post-CPB) were not different among the groups. Therefore, differences in latencies (see FIG. 4) is due to perturbations in cognition and not motor deficits.
Figure 6:
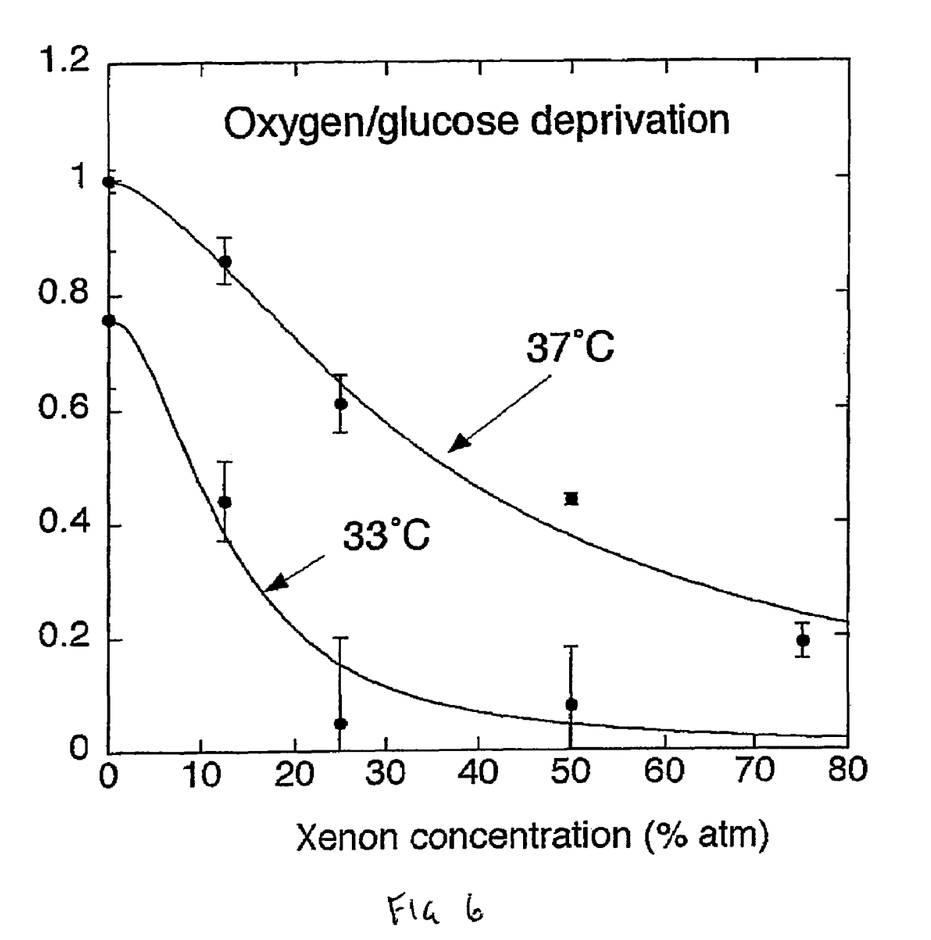
FIG. 6 shows the effects of xenon as a neuroprotectant at both normal body temperature (37° C.) and a lower temperature (33° C.). In more detail.

There was a statistically significant difference when each group was compared with CPB group (CPB vs Sham: F=18.2, p<0.0001; CPB vs CPB+MK801: F=20.7, p<0.0001; CPB vs CPB+Xe: F=21.6, p<0.0001). Repeated measurements with Student-Neman-Keuls showed a significant difference when compared with CPB group on 3rd and 4th day post-operatively (FIG. 4). Swimming speeds varied from 4.7 to 6.2 inch/sec throughout 10 postoperative days and no significant differences were found at the corresponding time points among the four groups (FIG. 5).

The above results clearly indicate that the administration of xenon during CPB imparts significant protection against neurocognitive and neuromotor deficits which follow bypass.

Temperature Variation Studies

The effects of xenon as a neuroprotectant were investigated at normal body temperature (37° C.) and at a lower temperature (33° C.), for example, as may pertain during CPB. The study was based on measuring LDH release from a mouse neuronal/glial co-culture in accordance with the method described in WO 01/08692 (in the name of Imperial College of Science, Technology and Medicine).

The data show that xenon reduces LDH release from a mouse neuronal/glial co-culture very effectively at 37° C., but surprisingly more effectively at 33° C. Indeed, xenon has an EC50 of 35.9+/−2.2% at 37° C. but only 11.5+/−2.0% at 33° C. This enhanced efficacy is unexpectedly higher than that predicted merely on the basis of simple physical chemistry; in other words, the enhanced efficacy is much greater than that attributable to the expected increase in binding affinity of xenon to its targets at lower temperatures.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in chemistry or related fields are intended to be within the scope of the following claims.

The invention claimed is:

1. A method of controlling one or more neurological deficits associated with cardiopulmonary bypass in a mammal, said method comprising administering to the mammal:
   (i) prior to the commencement of cardiopulmonary bypass a gaseous mixture comprising xenon, the xenon having a percent concentration by volume of between about 12.5% and 50%; and
   (ii) during cardiopulmonary bypass a gaseous mixture comprising xenon, the xenon having a percent concentration by volume of between about 12.5% and 50%.

2. The method according to claim 1, wherein xenon is administered in step (i) prior to commencement of cardiopulmonary bypass during preparatory surgery.

3. The method according to claim 1, wherein the one or more neurological deficits are selected from neuromotor or neurocognitive deficits.

4. The method according to claim 1, wherein the xenon is administered in combination with a pharmaceutically acceptable carrier, diluent or excipient.

5. The method according to claim 1, wherein the xenon is administered in the form of a 70 to 30% by volume xenon/oxygen mixture.

6. The method according to claim 1, wherein the xenon is administered in step (ii) intravenously.

7. The method according to claim 1, further comprising:
(iii) administering xenon to said mammal after cardiopulmonary bypass.

8. The method according to claim 7, wherein the xenon is administered in step (iii) as a gaseous mixture comprising a percent volume concentration of xenon between about 12.5% and 50%.

9. The method according to claim 7, wherein xenon is administered in step (iii) after the heart has been restarted; during the final stages of surgery; or after the heart has been restarted and during the final stages of surgery.

10. The method according to claim 7, wherein the xenon is administered in step (iii) via inhalation.

11. The method according to claim 7, wherein the xenon is administered in step (iii) intraveneously.

12. The method according to claim 11, wherein the xenon is administered in step (iii) as a liquid emulsion.

13. The method according to claim 1, wherein the xenon is administered during steps (i) and (ii) under hypothermic conditions.

14. The method according to claim 1, wherein the xenon is administered during steps (i) and (ii) under hypothermic conditions at a temperature of 33° C.

* * * * *